(12) United States Patent
Von Weymarn-Scharli

(10) Patent No.: US 8,523,786 B2
(45) Date of Patent: Sep. 3, 2013

(54) CONTROLLABLE STIFFNESS CATHETER GUIDE DEVICE

(76) Inventor: Alexander Von Weymarn-Scharli, Basel (CH)

( * ) Notice: Subject to any disclaimer, the term of this patent is extended or adjusted under 35 U.S.C. 154(b) by 362 days.

(21) Appl. No.: 12/800,019

(22) Filed: May 6, 2010

(65) Prior Publication Data

US 2010/0305477 A1 Dec. 2, 2010

Related U.S. Application Data

(62) Division of application No. 10/530,455, filed as application No. PCT/CH03/00556 on Aug. 19, 2003, now Pat. No. 7,736,323.

(30) Foreign Application Priority Data

| Oct. 15, 2002 | (CH) | ........................................ 1712/02 |
| Jun. 20, 2003 | (CH) | ........................................ 1083/03 |

(51) Int. Cl.
 *A61M 25/00* (2006.01)
 *A61B 5/00* (2006.01)
(52) U.S. Cl.
 USPC ........................... 600/585; 604/524; 604/525
(58) Field of Classification Search
 USPC ........................... 600/585; 604/523–528, 530
 See application file for complete search history.

(56) References Cited

U.S. PATENT DOCUMENTS

| 3,874,002 | A | * | 4/1975 | Kurpanek | .................... 623/3.22 |
| 4,838,859 | A | * | 6/1989 | Strassmann | ................ 604/95.03 |
| 4,869,656 | A | * | 9/1989 | Della Sala | .................... 417/412 |
| 5,337,733 | A | * | 8/1994 | Bauerfeind et al. | .......... 600/139 |
| 5,706,827 | A | * | 1/1998 | Ehr et al. | ....................... 600/585 |
| 5,895,404 | A | * | 4/1999 | Ruiz | .............................. 606/185 |
| 5,897,536 | A | * | 4/1999 | Nap et al. | ...................... 604/524 |
| 6,251,061 | B1 | * | 6/2001 | Hastings et al. | ................ 600/16 |
| 6,529,775 | B2 | * | 3/2003 | Whitebook et al. | .......... 607/101 |
| 2004/0054322 | A1 | * | 3/2004 | Vargas | ........................ 604/95.04 |
| 2008/0091170 | A1 | * | 4/2008 | Vargas et al. | ................. 604/528 |
| 2011/0166566 | A1 | * | 7/2011 | Gabriel | ............................ 606/34 |
| 2011/0282149 | A1 | * | 11/2011 | Vargas et al. | ................. 600/114 |

* cited by examiner

*Primary Examiner* — Rene Towa
*Assistant Examiner* — Adam Eiseman
(74) *Attorney, Agent, or Firm* — Adams & Wilks

(57) ABSTRACT

The invention relates to a guide device (1), in particular for positioning catheters in a body duct. The guide device (1) has an extended first thread (2) and at least one extended second thread (3) made from wire, which runs close to the first thread (2). According to the invention, the guide device (1) has a device (8), provided for one of the threads (2, 3) by means of which it is possible to actively control a relative movement between the threads (2, 3) or at least make the same difficult. The control device (8) is for example embodied such that the first thread (2), prepared from a flexible material, exerts a pressure, preferably acting a radial direction, on the several second threads, or that magnetic fields (4) of differing polarities along the first thread (2), prepared from a flexible material and along the second thread (3), may be generated for the selective introduction of an opposing attraction of the threads (2, 3) for reinforcing the guide device (1).

12 Claims, 4 Drawing Sheets

CONTROLLABLE STIFFNESS CATHETER GUIDE DEVICE

CROSS REFERENCE TO RELATED APPLICATIONS

This application is a division of U.S. application Ser. No. 10/530,455 filed Apr. 5, 2005 now U.S. Pat. No. 7,736,323, which is a U.S. national stage application of International Application No. PCT/CH2003/000556 filed Aug. 19, 2003, claiming priority of Swiss Application Nos. 1712/02 filed Oct. 15, 2002 and 1083/03 filed Jun. 20, 2003, and published in the English language.

BACKGROUND OF THE INVENTION

The invention relates to a guide device in particular for the positioning of catheters in a body duct.

The problem is addressed in WO 02/34324 A2, in which guide wires connect a section made of a superelastic material with a section made of steel which is significantly stiffer than the first-mentioned section. The guide wire known from WO 00/40288 A1 has a shapeable body on its distal section, the flexibility of which is changed continuously and should retain its shapeable characteristics.

The problem that the guide wire tends to be moved during the withdrawal of the catheter is addressed in EP 0 714 315 B1. The guide wire revealed here is designed in such a way that its movement is clearly recognizable visually.

The guide wire described in DE 200 19 484 U1 exhibits basic non-ferromagnetic bodies at regular intervals. They are furnished with minimum quantities of ferromagnetic particles, whereby the guide wire consists of a hollow cylindrical tube made of a non-ferromagnetic material such as plastic, for example. It contains a cylindrical carrier which is marked with clusters of ferromagnetic particles at regular intervals. This guide wire is especially suitable for processes controlled through magnetic resonance tomography.

A filter fixture which catches embolic material in a blood vessel and also envelopes a guide wire is known from DE/EP 0 980 278 T1. Furthermore, a catheter is known from the last-named publication, which has an expandable stent, whereby the stent exhibits a first diameter and also a second expanded diameter and also has an expandable frame which can be expanded between a contracted and an opened condition. Furthermore, the catheter has a sleeve, whereby the sleeve is pulled back during its use in order to free the expandable frame cavity and the stent. The expandable frame can exhibit a lumen seal.

The catheter furthermore has a pump system which exhibits a first lumen designed to accept fluid under pressure and a second lumen designed to evacuate gas. The inflation seal has furthermore an inlet opening with a fluid connection to the first lumen of the pump system and an exit opening with a fluid connection to the second lumen of the pump system. The inflatable seal can exhibit a hose-shaped balloon.

A guide wire with a core wire is described in EP 0 826 389 B1. It has a number of thin wires twisted with each other. The core wire has a semi-circular cross-section and through it makes room for a channel for fluid passage. The guide wire and core wire are part of a catheter, the forward end of which is open and thereby enables fluid discharge in the lengthwise direction of the catheter.

A guide wire which exhibits an outer tube which is shaped from a flexible material without restoring force is known from EP 0 823 261 A2. Furthermore, the guide wire has an inner core wire which can be moved back and forth in the outer tube. The core wire has a distal end which, although it is flexible on the one side, exhibits a return force on the other side, but in certain manner such as that if possible the distal end protrudes bent in a prescribed manner especially at the distal end of the outer tube. For this purpose, the distal end of the outer tube is formed very flexibly.

A guide wire unit is described in EP 0 778 044 A2. A sensor unit in a hollow, flexible component such as a hollow tube can slide into it in order to stiffen the flexible components. The sensor unit has a flexible sensor sleeve and an inner sensor wire, whereby the distal end of the latter is bent in advance in a certain manner. The sensor unit serves, for example, to stiffen an electrode cable during the insertion of the cable through a vein to the heart of the patient.

A catheter which exhibits two balloons arranged behind each other at its forward end for the dilation of vessels is known from NL-A-9 500 283. The balloons can be subject to a medium which is under pressure through connections.

A guide device, called a guide wire is known, for example, from DE 100 17 147 A1. This guide wire consists of an outer wire thread which is shaped as a hollow thread as well as an inner thread which can be moved inside it. The wire thread has a curved guide tip at its distal end. It acts as a control element or pathfinder during the insertion of the guide wire.

The guide devices or guide wires mentioned are introduced into a body duct, for example, in a vessel such as a vein or artery so that a catheter can later be pushed along the guide wire. Different, narrow branches are to be entered with the guide wire, whereby the relatively stiff catheter is to be introduced afterwards. In the case of the last-mentioned guide wire, the curvature is prescribed at its distal end, so that the corresponding pre-shaped guide catheter with the correct curvature is to be selected. The diameter of such a guide catheter is relatively large as it is used as an outer guide. In the second step, the actual therapy catheter, for example, a balloon catheter, is to be pushed in later through the hollow of the guide catheter. The external guide catheter is relatively thick in the forward area because of its curvature. Furthermore, there is the danger that the forward part of the guide wire can slip out of the intended vessel at a branch of the vessel when inserting a relatively rigid therapy catheter without the use of a guide catheter.

Another guide device is known from U.S. Pat. No. 5,337,733. This guide device comprises a chamber lying between an inner wall and an outer wall, which can be sealed to the outside. The outer wall is formed by a flexible hose. The inner wall is also formed by a hose which, in contrast to the outer wall, can be deformed in the radial direction to the inside when a guide is introduced in the chamber. Furthermore, the outer wall can lie against the inner wall through the evacuation of the intermediate chamber in order to make the guide device stiff. The outer wall and the inner wall can attach to each other through attachment elements.

The invention is based on the task of creating a guide device of the kind mentioned at the beginning, which can be handled easily and is, above all, adequately flexible on one side, but also adequately stiff on other side.

SUMMARY OF THE INVENTION

In accordance with the invention, the control device is finished in such a way that magnetic fields of different polarities can be generated along the first wire thread and along the second wire thread to cause mutual attraction of the wire threads at will. This has the advantage that the individual threads and thereby the guide device is extremely flexible on the whole as long as no magnetic field is generated while the guide device on the other hand is adequately stiff through the mutual attraction of the threads when the magnetic fields are generated. In this way, the guide device in accordance with the invention is adequately flexible on the one hand, for example, for the introduction of the device into a body duct and on the other hand adequately stiff when sliding the catheter along it afterwards, in particular in the area of a branch of the vessel, so that the danger that the guide device can slip out of the intended vessel is extensively excluded. Such a guide device therefore combines two rather contradictory characteristics, namely adequate flexibility on the one hand and adequate stiffness on the other hand, depending upon which characteristic is desired precisely during the handling of the guide device.

It is an advantage if the first wire thread and/or the second wire thread is made of a magnetizable material, especially from a weakly magnetizable material. It is possible through this to build up the magnetic fields as desired and also to be able to reduce them again depending upon the flexibility or stiffness which is necessary for the guide device in the practical application. In accordance with another further design of the invention, the first wire thread and/or the second wire thread is made of a non-magnetizable material and provided with a magnetizable coating, through which every individual wire thread can be manufactured from a variety of materials to be selected. It is accordingly not necessary to manufacture the entire wire thread out of magnetizable material. It can rather be adequate to provide only the outer jacket of a wire thread with a magnetizable coating so that such a wire thread is also magnetizable.

In accordance with an advantageous further design of the invention, the first wire thread and/or the second wire thread is finished as a solid body or as a hollow body. In the case that both wire threads are formed as hollow bodies, the control device preferably exhibits a magnetizable liquid which is found in every wire thread. In the last-mentioned case, the hollow body of every wire thread can consist completely of non-magnetizable material as the mutual attraction of the wire threads can be caused through the magnetizable liquid found in each hollow body.

It is an advantage if the previously-described magnetic fields can be generated through electrical currents, meaning through the application of an electrical voltage to the wire threads. The magnetic fields can then be generated on the basis of electric fields through simple switching of the electrical voltage on and off respectively. The magnetic fields can be generated electromagnetically or simply, as previously-mentioned, with the help of an electric current which flows through a conductor. The electrical fields and thereby also the magnetic fields can therefore be increased and decreased extremely quickly. An electrical voltage can be applied directly to the guide wire in a simple manner and without an intrusion into the body to be examined so that negative effects on the human or animal bodies to be examined are extensively excluded.

In accordance with a further design of the invention, the wire threads are arranged beside each other and parallel to each other, preferably twisted with each other. In an especially space-saving arrangement, the wire threads are arranged concentrically to each other, whereby one of the wire threads is preferably arranged centrally on the inside and the other wire thread is arranged in the shape of a spiral, radially to the outside, around the first one. A spiral-shaped outer wire thread contributes to especially good flexibility of the guide device, so that the latter, for example, can be bent with a relatively small radius.

In accordance with a preferred further design of the invention, the first wire thread is arranged centrally on the inside and several second wire threads are arranged around the outer circumference of the first wire thread, preferably uniformly spaced from each other. In this way, good flexibility of the guide device is established and, on the other side, adequate stiffness of the guide device is then established if the first wire thread and the second wire thread attract each other mutually.

It is an advantage if the wire threads are shaped in such a way that they lie flat against each other when a magnetic/electrical field is generated to produce mutual attraction. In this way, good contact is enabled between the wire thread and relative movement between the wire threads is extensively prevented with the fields at work, through which the stiffness of the entire guide device in the present curvature found in the body is improved.

In accordance with another further design of the invention, the magnetic fields can be generated permanently magnetically, whereby preferably every wire thread is polarized along its length and alternating oppositely in the radial direction. This form of implementation has the advantage that mutual attraction or repulsion respectively of the individual wire threads can be realized through a simple displacement of the wire threads relative to each other in the axial direction. As the polarization changes continuously along every wire thread, a slight axial displacement of the wire threads relative to each other can already cause the desired repulsion or attraction.

It is advantageous if the control device can enable a mutual contact or attachment of the basic surfaces of the wire threads facing each other preferentially in the form of teeth and a separation of the basic surfaces from each other through the introduction of a fluid under pressure, preferentially a liquid or a gas, in the gaps between the wire threads. It is possible to increase the friction between such surfaces strongly and thereby to extensively prevent relative movement between such wire threads through mutual contact or attachment of surfaces of the wire threads facing each other. On the other side, the guide device can be extremely flexible when the surfaces are separated from each other through the previously-named measures.

In accordance with a preferred further design of the invention, the mutual contact or attachment of the surfaces of the wire threads facing each other can be brought about through the removal of the fluid, preferably with the additional application of a vacuum. In this way, it is ensured that the individual wire threads, also after frequent use of the guide device, lie closely against each other and can thereby contribute to preventing relative movement between the wire threads. Under certain circumstances, this effect can already be achieved through the application of a vacuum to achieve mutual contact between the surfaces of the wire threads facing each other, without requiring a certain treatment or the provision of teeth on the basic surfaces facing each other.

Examples of the implementation of the object of the invention are explained more closely in the following with the help of the drawings, whereby all characteristics described and/or presented graphically comprise the object of the present invention by themselves or in any desired combination independently of their summary in the claims reference to them. The following are shown:

DETAILED DESCRIPTION OF THE INVENTION

Figure 1:
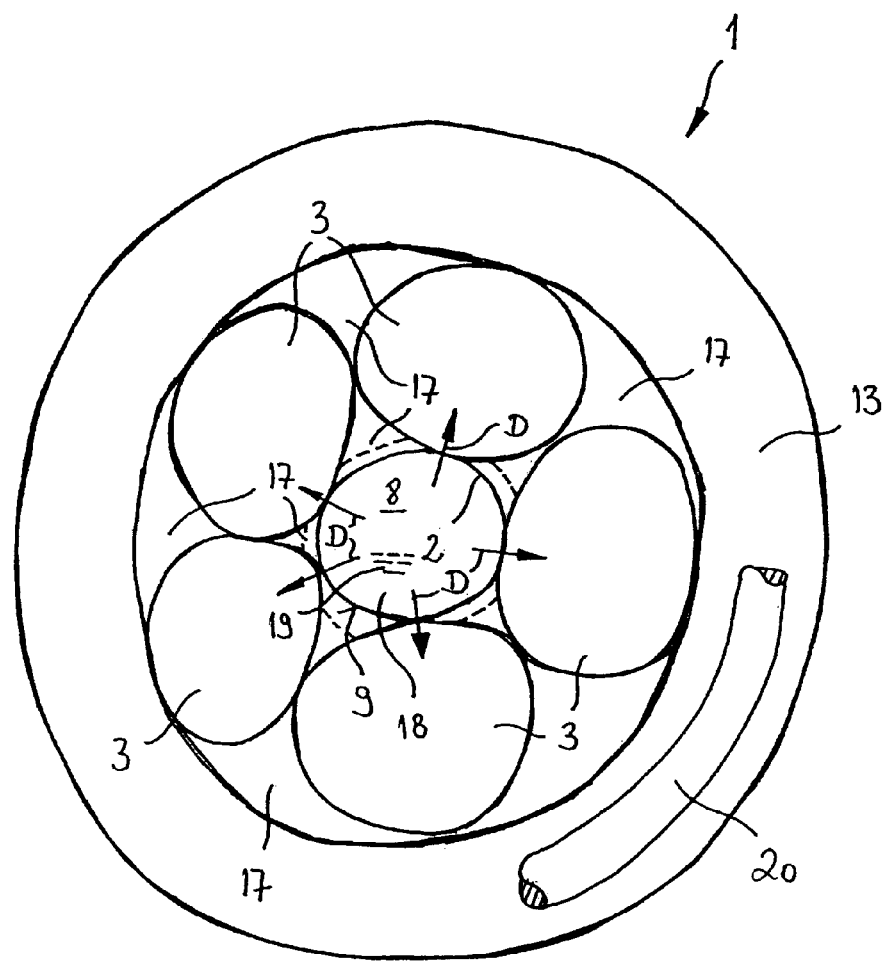
FIG. 1 A schematic, highly enlarged cross-section through a guide device, in particular for the positioning of catheters in a body duct, in accordance with a form of implementation not belonging to the invention.

At first, it is to be noted that the shading symbolizing a cross-section has been omitted in FIG. 1 for better overview.

A schematic cross-section of a guide device 1 is shown in FIG. 1. The guide device 1 is finished in accordance with a form of implementation not belonging to the scope of the invention. The guide device 1 has one first thread 2 in the form of an elongate hollow body, such as a central hose or balloon in accordance with this form of implementation. It is manufactured from a stretchable, elastic material and closely surrounded on its outer circumferential surface 9 by several second threads 3 in the form of elongate bodies made of wire while leaving a spiral cavity 17. There are five second threads 3 arranged in side-by-side relation with one another around the outside circumferential surface 9 of the first thread 2 in the form of implementation shown in FIG. 1. The second threads 3 are surrounded closely by an outer flexible sleeve 13 which is preferably manufactured from a material which cannot stretch or can stretch slightly in accordance with the form of implementation shown.

It is clear that the view shown in FIG. 1 represents a strong enlargement of the guide device 1 in accordance with the invention. It is furthermore clear that fewer or more than five second threads 3, each of which is finished as a wire thread can be foreseen.

A device 8 is connected to the threads 2 and 3, through which relative movement between the threads can be permitted or extensively impeded. The control device 8 is finished in such a way that the first thread 2 in its stretched condition, indicated with dashed lines in FIG. 1, exercises a radially outward effective pressure in accordance with FIG. 1 (as shown by the Arrows D) and presses the second threads 3 against the inner wall of the sleeve 13, flattening the threads 3 and pressing them sideways against one another. For this purpose, a fluid 19, preferably a liquid, under pressure can be applied to the cavity 18 of the first thread 2, namely the hose or balloon, using the control device 8. The fluid 19 is only indicated schematically in FIG. 1. It is clear that the fluid usually completely fills the cavity 18 of thread 2.

As indicated in FIG. 1, the first thread 2 and several second threads 3 are already in side-by-side contact with each other in the non-stretched condition of the first thread 2, and also the second threads 3 amongst each other. In the stretched condition of the first thread 2 indicated with dashes in FIG. 1, the first thread 2 and several second threads 3 as well as the second threads amongst themselves preferably lie flat against each other.

Furthermore, it is indicated in FIG. 1 that the outer sleeve 13 contains a spiral wire 20 wound in the lengthwise direction, only a part of which is shown in FIG. 1.

Figure 2:
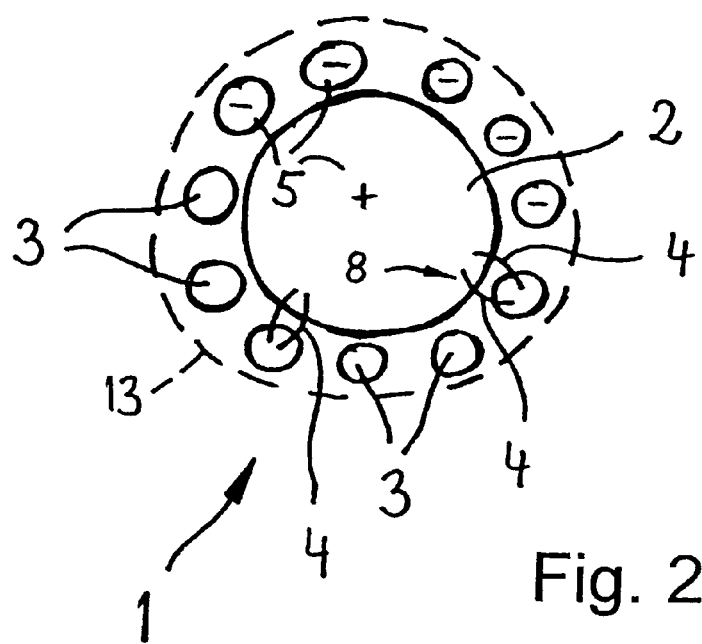
FIG. 2 A schematic, highly enlarged cross-section through a guide device, in particular for the positioning of catheters in a body duct, in accordance with a form of implementation in accordance with the invention.
Figure 3:
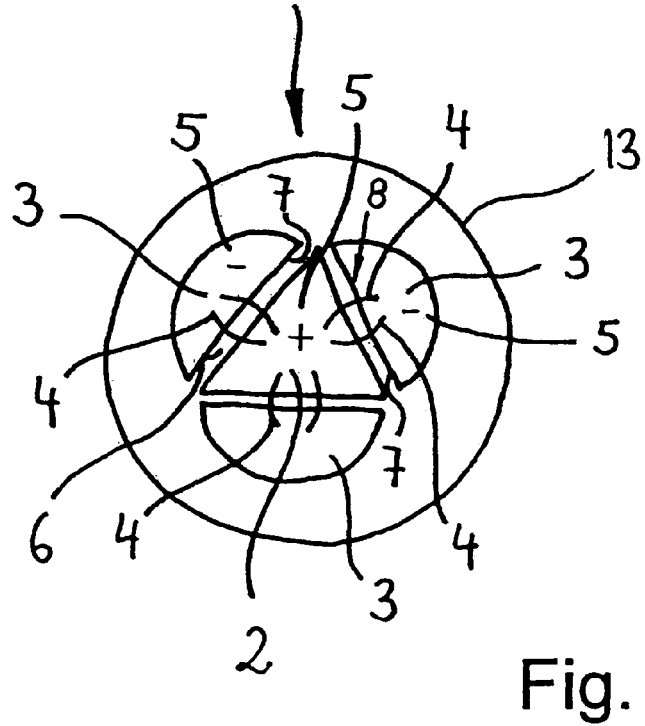
FIG. 3 A schematic, highly enlarged cross-section through a guide device, in accordance with a further form of implementation in accordance with the invention.
Figure 4:
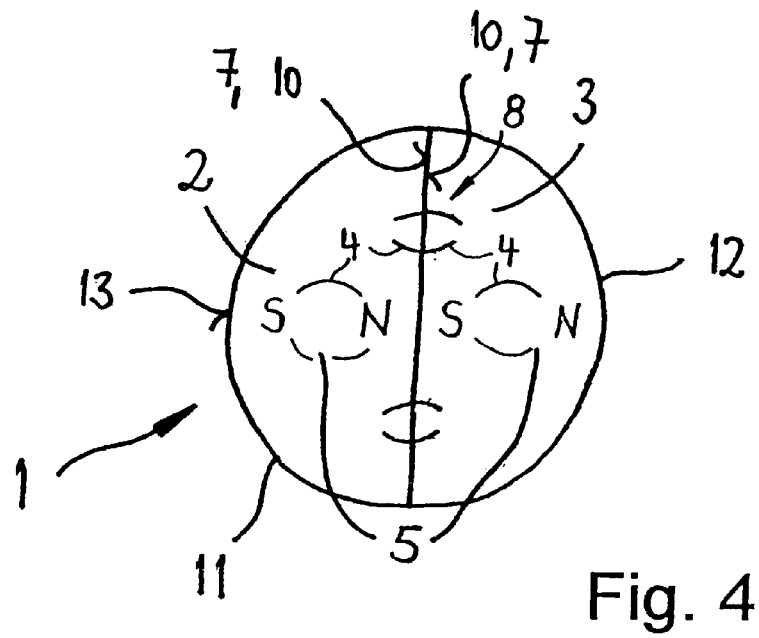
FIG. 4 A schematic, highly enlarged cross-section through a guide device in accordance with another form of implementation in accordance with the invention.
Figure 7:
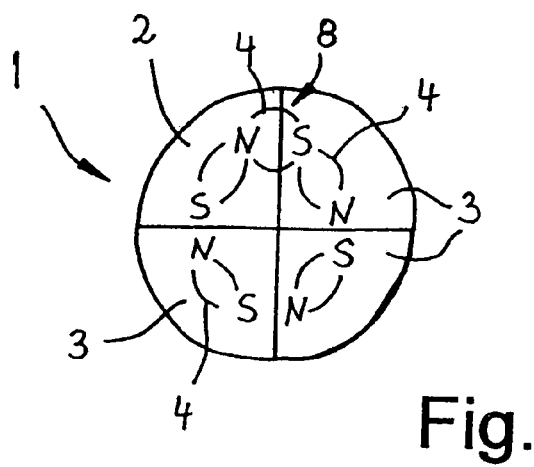
FIG. 7 A schematic cross-section through a guide device in accordance with a further form of implementation.

Furthermore, it is to be noted that the shading symbolizing a cross-section has been omitted in FIG. 2 through 4 as well as FIG. 7 for better overview and that the term "wire" is used here in a general, comprehensive sense for a long, thin body of any particular material.

Figure 8:
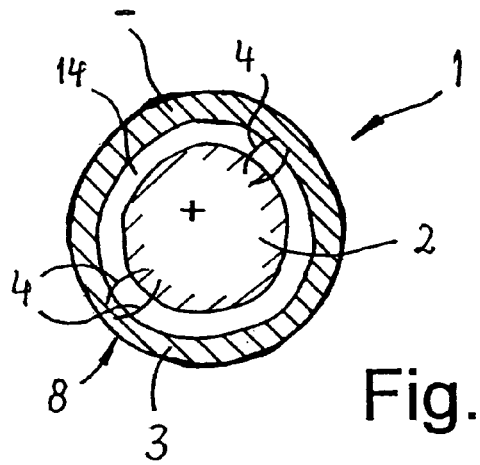
FIG. 8 A schematic cross-section through a guide device in accordance with another form of implementation.
Figure 9:
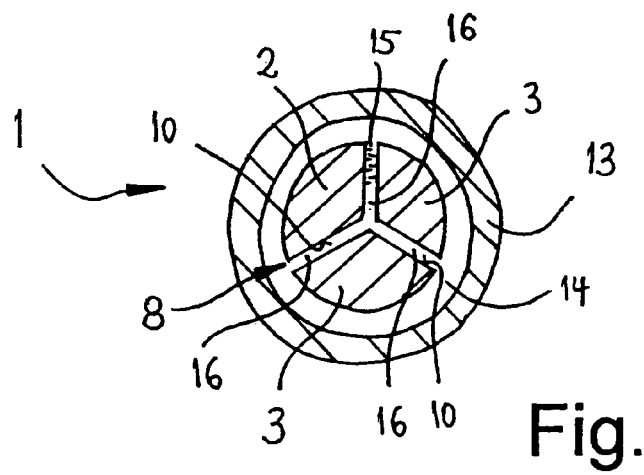
FIG. 9 A schematic cross-section through a guide device in accordance with a further form of implementation.

Cross-sections through various forms of implementation of a guide device 1 in accordance with the invention in particular for the positioning of catheters not drawn more closely in a body duct not presented are presented in FIG. 2 through 4 as well as FIG. 7 through 9. The guide device is shaped in the form of a so-called guide wire in each particular case here. The catheters are, for example, tubes made of metal, glass, plastic or rubber for introduction into body organs, such as, for example, the gall bladder, in order to drain, fill, rinse or examine the latter. The body duct is, for example, a vessel of a human or animal body, such as, for example, a vein or an artery.

The threads 2 and 3 are called wire threads in the following. The guide device 1 has a lengthwise first wire thread 2 and at least one lengthwise second wire thread 3 which runs near the first wire thread 2. In the example in accordance with FIG. 2, there are 11 second wire threads 3, in the example in accordance with FIG. 3 three second wire threads 3, in the example in accordance with FIG. 4 one second wire thread 3, in the example in accordance with FIG. 7 three wire threads 3, in the example in accordance with FIG. 8 one second wire thread 3, and in the example in accordance with FIG. 9 two second wire threads 3.

In accordance with the invention, a device 8 is connected to the wire threads 2 and 3. Through it, the possibility to permit relative movement between the wire threads 2 and 3 or at least to make it more difficult can be controlled purposefully. This device 8 is called the control device in the following.

The control device 8 is finished in such a way in accordance with the invention that magnetic fields 4 of different polarity 5 can be generated along the first wire thread 2 on the one side and along the second wire thread 3 on the other side to bring about a mutual attraction of the wire threads 2 and 3 at will. The fields 4 or forces which can be built up or decreased respectively are indicated only schematically in FIG. 2 through 8, whereby it is clear that fields of this kind exist between every first wire thread 2 and every second wire thread 3 provided that these fields are generated. The different polarity 5 of a first wire thread 2 and a second wire thread 3 is, for example, shown through the identification mark "+" or "−" in FIGS. 2 and 3 as well as FIG. 8 and through the letters "N" and "S" in FIG. 4 through 7, whereby "+" and "−" stand for positive and negative electrical charges respectively and "N" for the north pole and "S" for the south pole of a magnetic field.

In accordance with one form of implementation, the first wire thread and the second wire thread or the first wire thread or the second wire thread is manufactured from a magnetizable material, in particular a weakly magnetic material. In accordance with another form of implementation, the first wire thread and the second wire thread or the first wire thread or the second wire thread is manufactured from a non-magnetizable material and provided with a magnetizable coating 7 on its surface, whereby it is possible to apply the coating only in the areas of wire threads 2 and 3 which face toward the other wire thread in each case. These are, for example, the basic surfaces 6 of the cylinder segment-shaped second wire threads 3 in the case of the form of implementation in accordance with FIG. 3. The magnetizable coating 7 can be provided on the basic surfaces 10 of the cylinder halves 11 and 12 in the example in accordance with FIG. 4.

In accordance with the examples presented, the first wire thread 2 and/or the second wire thread 3 is shaped as a solid body (see FIG. 2 through 4 and FIG. 7) or as a hollow body (see FIGS. 8 and 9 with respect to the second wire thread 3).

In accordance with a form of implementation of the invention not presented, it is possible, in the case that both wire threads are shaped as hollow bodies, for a magnetizable fluid to be present in each wire thread so that mutual attraction of the wire threads arranged beside each other or arranged concentrically inside each other is possible with the application of magnetic fields. A magnetizable fluid is, for example, a colloidal, especially a stabilized suspension of magnetic or magnetizable particles. Most often, particles of about 10 nm are used. They are prevented from grouping together under the effects of the magnetic interactions by enveloping them with a surface-active substance such as oleic acid, for example. Water, but also oils and various other solvents can serve as a carrier fluid. A magnetizable fluid can be held fixed in every position through a magnetic field. This technical effect can also be used to stiffen a guide device.

The magnetic fields 4 can be generated through the application of a not-shown electrical voltage on wire threads 2 and 3 or on the magnetizable coating 7 respectively.

The wire threads 2 and 3 are arranged beside each other and parallel to each other in accordance with FIG. 2 through 7. In FIG. 7, a schematic cross-section is shown through a further form of implementation of a guide device 1, in which the form of implementation in accordance with FIG. 4 is cut in half once again, so that the individual wire threads 2 and 3 are also located beside each other and parallel to each other in this form of implementation.

In accordance with a form of implementation not shown more closely, it is also possible to twist the wire threads 2 and 3 around each other.

In accordance with a form of implementation shown in FIG. 8, the wire threads 2 and 3 are arranged concentrically to each other, whereby the first wire thread 2 is located at the middle on the inside of the second wire thread 3 which is shaped as a hollow body.

In accordance with a further form of the invention not shown more closely, one of the wire threads, the first wire thread 2, for example, is arranged centrally located on the inside and the other of the wire threads, the second wire thread 3, for example, is arranged spiral-shaped radially to the outside around the first one.

As indicated in the form of implementation shown more closely in FIG. 2, the first wire thread 2 is arranged centrally on the inside and provided with a circular-shaped cross-section. Several second wire threads 3 are arranged around the outer circumference of the first wire thread, spaced uniformly from each other in the example selected. As an example, eleven second wire threads 3 are foreseen in the form of implementation in FIG. 2. They also exhibit a circular-shaped cross-section in each case, whereby the diameter of the first wire thread 2 is selected significantly larger than that of the second wire threads 3 and the spacing between the second wire threads 3 and the first thread 2 is significantly smaller than the distance to the neighboring second wire threads 3 in each case.

In the form of implementation shown in FIG. 3, the first wire thread 2 has a cross-section in the form of a equilateral triangle, while the basic surface 6 of each of the second wire threads 3 in this example is shaped in such a way that the width of the basic surface 6 corresponds approximately to the length of one of the sides of the triangle in the cross-section of the first wire thread in the form of an equilateral triangle. The second wire threads 3 are shaped partly cylindrically or as cylinder segments. The wire threads 2 and 3 are surrounded in accordance with the forms of implementation of FIGS. 2 and 3 furthermore of an outer sleeve 13, which is only indicated with dashes in FIG. 2.

In the form of implementation presented in FIG. 4, the first wire thread 2 and the second wire thread 3 are shaped approximately identically with each other and shaped as half-cylinders. The two halves of the cylinder 11 and 12 thereby lie flat against each other and produce a circular-shaped cross-section in their assembled or pressed together condition. In this case, the individual wire threads 2 and 3 are also enveloped preferably by an outer sleeve 13.

Figure 5:
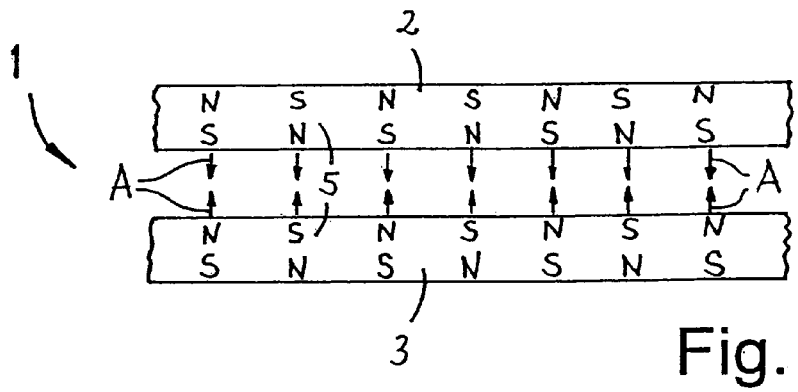
FIG. 5 A schematic top view of a guide device in accordance with FIG. 4, in which the two wire threads are represented spaced apart from each other.

In accordance with the forms of the invention presented in FIG. 4 through 7, the magnetic fields 4 can be generated within each wire thread and also from one wire thread to the other permanently magnetically, whereby, as shown in detail in a top view in FIG. 5 of the guide device 1 in accordance with FIG. 4, in which the individual wire threads are nevertheless separated from each other, each wire thread 2 and 3 is alternately oppositely polarized along its length and in the radial direction. A mutual attraction of the wire threads 2 and 3 results from this with the axial arrangement of the wire threads 2 and 3 in accordance with FIG. 5 as this is emphasized through the arrows A directed at each other in FIG. 5.

Figure 6:
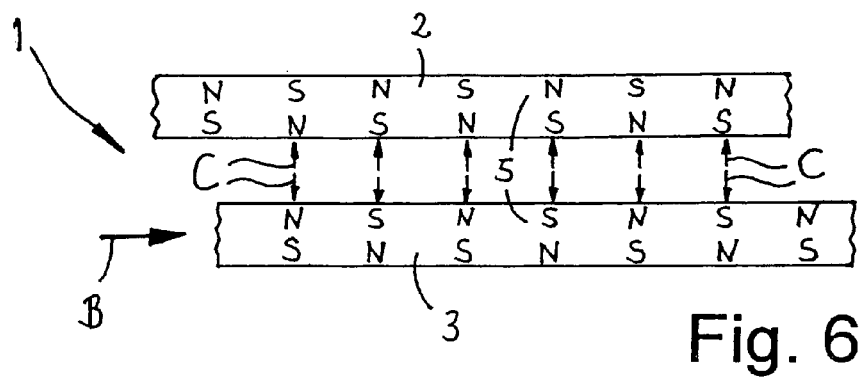
FIG. 6 A schematic top view of the guide device drawn in FIG. 4, in which the two wire threads are presented spaced apart from each other and displaced relative to each other.

If the second wire thread 3 is now moved in the direction of arrow B relative to the first wire thread 2 in the axial direction as indicated in FIG. 6, the wire threads 2 and 3 repel each other as the same polarities lie opposite each other in the wire threads. This is emphasized by the arrows C directed away from each other in FIG. 6. It is clear that the effect of the repulsion of the wire threads shown in FIG. 6 can also be achieved beginning with the arrangement in accordance with FIG. 5 in such a way that the first wire thread 2 is moved relative to the second wire thread 3 in the axial direction.

In the form of implementation shown in FIG. 7, the individual wire threads 2 and 3 have the shape of quarter cylinders and are almost identically shaped, so that four wire threads facing each other and touching each other produce a circular cross-section. In this form of implementation, the individual polarities are also emphasized through the abbreviations "N" and "S" with the magnetic fields 4 which run within each wire thread, but then also from one wire thread to the other.

The individual wire threads 2 and 3 could also be moved relative to each other in the axial direction analogous to the form of implementation illustrated in FIGS. 5 and 6 through which, as indicated in FIG. 6, the same polarities can result in wire threads located opposite each other so that the wire threads repel each other. In this respect, the wire threads 2 and 3 in the forms of implementation of FIG. 4 through 7 are shown in the form of permanent magnets.

In the case of another example, the wire threads 2 and 3 can also exhibit a circular-shaped cross-section in each case and be arranged beside each other (not shown), whereby the surfaces of these wire threads facing toward each other can also be finished in such a way that not a line-shaped contact, but rather a surface contact of the wire threads is possible in case of mutual attraction of the wire threads.

It is clear that the relative spacing of the first wire threads to the second wire threads as well as the second wire threads to each other, if several are available, are represented highly enlarged relative to each other in FIG. 2 through 9 and that especially with the examples of implementation in FIGS. 2 and 3, the outer sleeve 13 can also lie closely on the second wire threads 3.

In the form of implementation of the invention shown in FIG. 8, the first wire thread 2 has a circular-shaped cross-section and is located in the second wire thread 3, which is finished with the shape of a pipe with a ring-shaped cross-section area. With this form of implementation as well, it is clear that the spacing shown between the first wire thread 2 and the second wire thread 3 is highly enlarged and that in practice the outside diameter of the first wire thread 2 is only slightly smaller than the inside diameter of the second wire thread 3. If desired, a lubricating fluid can also be located in the ring-shaped interior cavity 14 between the first wire thread 2 and the second wire thread 3. But, it is also possible to do without such a lubricating fluid.

A further form of implementation of the guide device 1 is presented in a schematic cross-section in FIG. 9. Three wire threads, namely a first wire thread 2 and two second wire threads 3 which have approximately identical cross-sections are located in the outer sleeve 13. In this form of implementation, the control device 8 is finished in such a way that it enables mutual contact or attachment of the basic surfaces 10 facing each other, preferably in the form of teeth 15 indicated only schematically in FIG. 9, for example, in the form of fine little hairs located on the basic surfaces of the wire threads 2 and 3 facing each other and that a separation of the basic surfaces 10 from each other is enabled through the introduction of a fluid, preferably a liquid or gas, under pressure into the gap 16 between the wire threads 2 and 3. The fluid can equally well be introduced into the ring-shaped inner chamber 14 between, wire threads 2 and 3 and the outer sleeve 13. The mutual contact or attachment of the basic surfaces 10 of the wire threads 2 and 3 facing each other and finished as a partial cylindrical form can be brought about, for example, through the removal of the fluid, preferentially with the application of a vacuum in addition.

In the case of the forms of implementation shown in FIG. 3 through 8, the wire threads 2 and 3 are shaped in such a way that they contact each other with their surfaces and can thereby contribute to an outstanding possibility of stiffening the guide device 1 with the generation of a magnetic field 4. It is clear that the first wire thread 2 and the second wire thread 3 can be charged positively or negatively to generate the magnetic fields which are necessary to bring about a mutual attraction of the wire threads. The stiffening of the guide device 1 is achieved through the mutual attraction of the wire threads. Such a stiffening is possible in the particular position of the guide device which the wire assumes just then in the particular body duct.

The guide device 1 or guide wire has the ability not to twist without further ado; it is therefore torsion-rigid. It furthermore exhibits a resistance to bending, the ability to push and not to kink. It is adequately flexible and can slide. It has a diameter, for example, of 0.9 or 1 mm. In this way, the guide device in accordance with the invention can be handled without having to make a larger additional hole with respect to the cross-section of the guide device. Furthermore, there is extensive flexibility with respect to the materials selected for the wire threads of the guide device. All usual catheters can be used with the guide device in accordance with the invention. Handling is safe and simple.

The guide device in accordance with the invention can, as mentioned, be used in particular for the positioning of catheters in a body duct. It is also possible to use such a guide device in industrial engineering where thicker guide units can be used if necessary.

In this way, a guide device which is adequately flexible on the one hand but also adequately stiff on the other hand has been created so that the guide device in accordance with the invention can be handled easily.

The invention claimed is:

1. A guide device for positioning a catheter in a body duct, the guide device comprising:
a flexible sleeve configured for insertion to a body duct;
a long first wire thread disposed inside the flexible sleeve;
at least one long second wire thread which is disposed inside the flexible sleeve and which runs close to the first wire thread; and
a control device connected to the wire threads and configured to control relative movement between the wire threads,
wherein the control device generates magnetic fields of different polarities along the first wire thread and along the second wire thread to bring about a mutual attraction of the wire threads to enable mutual contact or attachment to each other of surfaces of the wire threads facing each other, and
wherein the control device is configured to introduce a fluid under pressure in a gap between the wire threads to enable separation of the surfaces of the wire threads from each other.

2. A guide device according to claim 1; wherein the first wire thread and/or the second wire thread is manufactured from a magnetizable material or is manufactured from a non-magnetizable material and provided with a magnetizable coating.

3. A guide device according to claim 1; wherein the magnetic fields are generated through the application of electric voltage to the wire threads.

4. A guide device according to claim 1; wherein the first wire thread is arranged centrally on the inside and several second wire threads are arranged around the outer circumference of the first wire thread.

5. A guide device according to claim 1; wherein the mutual contact or attachment of the surfaces of the wire threads facing each other is brought about through the removal of the fluid.

6. A guide device for guiding a therapy catheter in a body duct, comprising: a flexible sleeve dimensioned to be inserted into a body duct; a first elongate body and one or more second elongate bodies disposed inside the sleeve in side-by-side relation and extending lengthwise along the sleeve; and means for selectively creating magnetic attraction and repulsion forces between the first body and the one or more second bodies to vary the stiffness of the guide device.

7. A guide device according to claim 6; wherein the first body is disposed at the center of the sleeve and plural second bodies are disposed around the outer circumference of the first body; and wherein the means for selectively creating magnetic attraction and repulsion forces comprises means for creating magnetic fields of opposite polarity along the lengths of the first body and the second bodies.

8. A guide device according to claim 7; wherein the second bodies are movable into and out of contact with the first body in response to the magnetic attraction and repulsion forces.

9. A guide device according to claim 6; wherein the first body and the one or more second bodies are hollow bodies; and wherein the means for selectively creating magnetic attraction and repulsion forces comprises a magnetizable fluid inside each hollow body, and means for creating magnetic fields of opposite polarity that interact with the magnetizable fluid along the lengths of the first body and the one or more second bodies.

10. A guide device according to claim 6; wherein the means for selectively creating magnetic attraction and repulsion forces comprises forming the first and second bodies of permanent magnets that are alternately oppositely polarized along their lengths, and wherein the first body is movable lengthwise relative to the one or more second bodies to vary the magnetic attraction and repulsion forces.

11. A guide device according to claim 6; wherein the first and second bodies are comprised of magnetizable material or have a coating of magnetizable material.

12. A guide device according to claim 6; wherein the first and second bodies are concentric to one another.

* * * * *